(12) United States Patent
Schlüter et al.

(10) Patent No.: US 8,637,812 B2
(45) Date of Patent: Jan. 28, 2014

(54) SAMPLE EXCITATION APPARATUS AND METHOD FOR SPECTROSCOPIC ANALYSIS

(75) Inventors: Hans-Jürgen Schlüter, Bremen (DE); Robert Malek, Lilienthal (DE)

(73) Assignee: Thermo Fisher Scientific (Bremen) GmbH, Bremen (DE)

( * ) Notice: Subject to any disclaimer, the term of this patent is extended or adjusted under 35 U.S.C. 154(b) by 491 days.

(21) Appl. No.: 12/810,222

(22) PCT Filed: Dec. 23, 2008

(86) PCT No.: PCT/EP2008/011097
§ 371 (c)(1),
(2), (4) Date: Jun. 23, 2010

(87) PCT Pub. No.: WO2009/083242
PCT Pub. Date: Jul. 9, 2009

(65) Prior Publication Data
US 2010/0271631 A1    Oct. 28, 2010

(30) Foreign Application Priority Data
Dec. 27, 2007  (GB) .................................. 0725274.5

(51) Int. Cl.
*H01J 49/04*    (2006.01)
*H01J 49/10*    (2006.01)
*G01J 3/30*     (2006.01)

(52) U.S. Cl.
USPC ............................ 250/288; 250/282; 356/315

(58) Field of Classification Search
USPC ................. 250/288, 285, 281, 282, 287, 292; 356/326
See application file for complete search history.

(56) References Cited

U.S. PATENT DOCUMENTS

| | | | | |
|---|---|---|---|---|
| 5,192,865 A | * | 3/1993 | Zhu ............................... | 250/288 |
| 5,247,842 A | * | 9/1993 | Kaufman et al. ............. | 73/865.5 |
| 6,126,086 A | * | 10/2000 | Browner et al. ............ | 239/102.1 |
| 6,265,717 B1 | * | 7/2001 | Sakata et al. .................. | 250/289 |
| 6,541,768 B2 | * | 4/2003 | Andrien et al. ................ | 250/288 |
| 6,614,021 B1 | * | 9/2003 | Kalinitchenko ............... | 250/294 |
| 6,649,907 B2 | * | 11/2003 | Ebeling et al. ................ | 250/288 |
| 6,727,497 B2 | * | 4/2004 | Scalf et al. .................... | 250/288 |
| 6,774,359 B1 | * | 8/2004 | Hirabayashi et al. ......... | 250/287 |
| 7,005,635 B2 | * | 2/2006 | Ahern et al. .................. | 250/288 |
| 7,378,652 B2 | * | 5/2008 | Ahern et al. .................. | 250/288 |

(Continued)

FOREIGN PATENT DOCUMENTS

WO    WO 2007/008191 A1    1/2007

*Primary Examiner* — Sang Nguyen
(74) *Attorney, Agent, or Firm* — Charles B. Katz

(57) ABSTRACT

Sample excitation apparatus for a spectrometric analyzer, the apparatus comprising a sample introduction stage comprising an electrospray nebulizer for generating a nebulized sample; and a sample excitation stage arranged to operate in an atmospheric pressure environment and to receive and excite the nebulized sample in a sample excitation region for spectrometric analysis thereof. 'Excitation' includes ionization in ICP and MIP, flame excitation in AES, and optical excitation in AAS. For example, analyte solution (38) is fed out of the outlet end of a capillary (30,40,60,96), to a plasma source. A potential difference is applied between the capillary, its outlet end or the analyte solution and an opposing effective (counter) electrode, which may comprise a tube (64), a grid (80), or the plasma (34) itself, to promote formation of smaller droplets (46). The pressure of the plasma source is similar to the pressure in the region of the capillary outlet end.

25 Claims, 3 Drawing Sheets

(56) References Cited

U.S. PATENT DOCUMENTS

| | | |
|---|---|---|
| 2002/0060288 A1* | 5/2002 | Hughey et al. ............... 250/281 |
| 2003/0106996 A1* | 6/2003 | Covey et al. ............... 250/288 |
| 2003/0136904 A1 | 7/2003 | Mukaibatake |
| 2003/0213907 A1* | 11/2003 | Rutzke et al. ............... 250/288 |
| 2005/0072934 A1 | 4/2005 | Frazer et al. |
| 2005/0269518 A1* | 12/2005 | Bajic et al. ............... 250/423 F |
| 2007/0102634 A1* | 5/2007 | Frey et al. ............... 250/288 |
| 2007/0138406 A1 | 6/2007 | Mordehai |

* cited by examiner

SAMPLE EXCITATION APPARATUS AND METHOD FOR SPECTROSCOPIC ANALYSIS

FIELD OF THE INVENTION

This invention relates to a sample excitation apparatus and method for supplying and exciting a sample in a plasma generator, a flame, or another sample excitation device for subsequent spectroscopic analysis of the sample. In particular, the invention finds application in the following elemental analysis techniques, among others: inductively coupled plasma mass spectrometry (ICP-MS), microwave induced plasma mass spectrometry (MIP-MS), plasma optical (or atomic) emission spectroscopy (ICP/MIP-OES/AES, in particular using the iCAP ICP spectrometer manufactured by Thermo Fisher Scientific Inc.), atomic emission spectroscopy (AES) and atomic absorption spectroscopy (AAS). In all of the above techniques, the sample ionisation/excitation device is arranged to operate in an atmospheric pressure environment.

BACKGROUND OF THE INVENTION

Sample introduction apparatuses in the form of nebulisers for liquid samples are known. For example, pneumatic nebulisers, ultrasonic nebulisers, and thermospray nebulisers have been coupled to ICP-MS instruments. A nebuliser converts a liquid sample into a spray, or aerosol, which is directed to a plasma/excitation device, either for ionisation for mass spectrometry analysis downstream of the device, or for excitation for optical emission/absorption analysis in the device.

Figure 1:
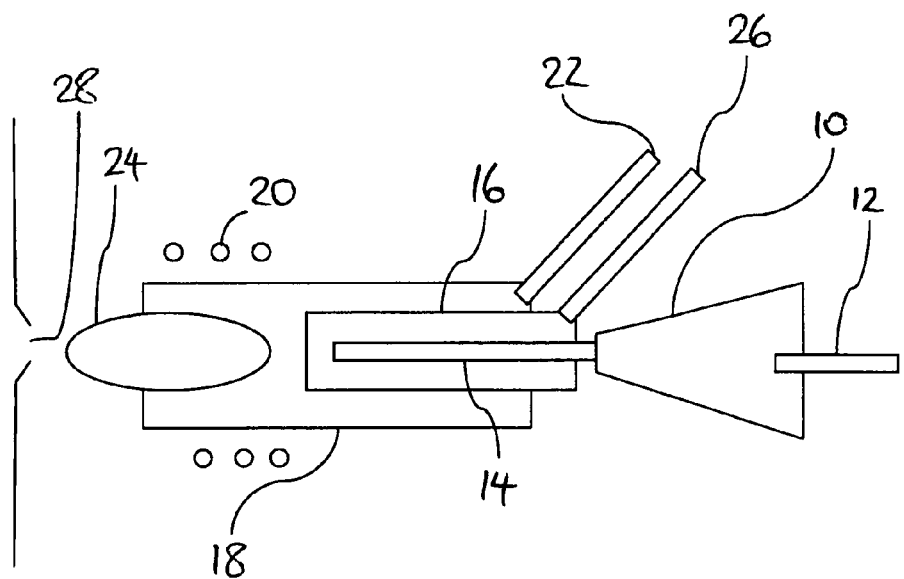

FIG. 1 shows schematically conventional ICP-MS source. A liquid is introduced into a spray chamber 10 using a nebuliser 12, which is typically driven by a flow of the same gas as the plasma gas (usually argon but sometimes helium). The spray chamber 10 may optionally incorporate a line-of-sight obstruction (not shown), to prevent direct delivery of droplets into a sample tube, or injector, 14. It may also optionally incorporate a drain (not shown) for removal of excess liquid and a cooling device (not shown). The sample tube 14 is disposed within an auxiliary gas tube 16, which is itself disposed inside a plasma torch 18. Such a torch is shown in U.S. Pat. No. 7,273,996. Surrounding the torch 18 is an induction coil 20 which is energised with an RF electric current, typically at 27 or 40 MHz. A plasma gas—typically argon—is supplied via a plasma gas inlet 22 into the torch 18 and is converted into a plasma at a plasma region 24 towards the end of the torch. The aerosol enters the torch 18 via the sample tube 14 and auxiliary gas tube 16 and, due to the high temperature of the plasma, is ionised at the plasma region 24. To help to introduce the nebulised sample into the centre of the plasma region, an auxiliary gas flow is provided via an auxiliary gas inlet 26 into the auxiliary gas tube 16, so that both the plasma gas and the auxiliary gas surround the sample stream concentrically. Finally, the sample ions are extracted from the plasma through a sampling aperture 28, to a mass analysing apparatus.

In ICP-OES, a similar configuration is used, except that the sampling aperture 28 is not required, since extraction to a mass spectrometer does not take place. Instead, optical emissions from the sample in the plasma region 24 are analysed with an optical spectrometer. Observations with the spectrometer may be made from the back or from the side of the plasma region.

It is known that the efficiency of sample ionisation or of sample excitation for emission/absorption is affected by the size and distribution in size of the sample droplets resulting from nebulisation. Large droplets and a wide distribution in droplet size lead to excessive liquid injection into the torch and consequentially instability of the plasma due to the varying load. Contamination of the sample and skimmer cones may also increase. Furthermore, because of the increased energy requirement for evaporating larger droplets, incomplete atomisation and ionisation of the sample may occur, resulting in molecular interferences.

A general approach for improving the stability of the plasma is to increase the size and power of the plasma generator, to cope with large sample droplets and variations in the droplet size. Another approach involves cooling the nebulisation spray chamber, to provide condensed droplets on its walls. This leads to a shift of the liquid/gaseous equilibrium in the spray chamber, resulting in smaller droplets, by the removal (evaporation) of solvent from the droplets to bring the partial pressure of the solvent back towards its required vapour pressure in the spray chamber as solvent condenses and is drained away.

A further approach involves providing a small diameter for the nebuliser needle bore, with the aim of providing smaller droplets into the spray chamber. However, since ICP samples frequently have a high salt content and comprise a certain proportion of unsolvated solid, precipitation of salts in the needle can result, eventually leading to blockage of the bore. Consequently, the bore diameter cannot be made very small and an additional, desolvation or dehumidification step may be introduced to try to reduce the nebulised droplet size.

The above techniques for nebulisation and desolvation involve costly spray chambers and spray chamber cooling, as well as the provision of an argon flow which may exceed what is actually needed for clean driving of the plasma itself. Despite the various developments discussed above, there is considerable room for improvement in the droplet formation technique.

There is a need therefore for an improved or alternative sample excitation apparatus and method for supplying and exciting a sample in a plasma generator, a flame, or another sample excitation device for subsequent elemental analysis thereof. In particular, it would be desirable to provide a sample excitation apparatus which comprises a standard ICP ionisation source. This invention aims to provide such an apparatus and method.

SUMMARY OF THE INVENTION

According to a first aspect of the invention, there is provided a sample excitation apparatus for a spectrometric analyser, the apparatus comprising: a sample introduction stage comprising an electrospray nebuliser for generating a nebulised sample; and a sample excitation stage arranged to operate in an atmospheric pressure environment and to receive and excite the nebulised sample in a sample excitation region for spectrometric analysis thereof.

The term "excitation" covers, for example, ionisation in ICP and MIP, flame excitation in AES, and optical excitation in AAS, among others.

Preferably, the electrospray nebuliser is arranged to discharge the nebulised sample directly into the sample excitation region. Alternatively, the sample introduction stage may comprise a spray chamber and the electrospray nebuliser may be arranged to discharge the nebulised sample into the spray chamber. Alternatively still, the sample introduction stage may comprise an auxiliary gas tube and the electrospray nebuliser may be arranged to discharge the nebulised sample into the auxiliary gas tube.

Either way, it is preferable for a counter electrode to be configured as part of, or at, the sample excitation region, the spray chamber, or the auxiliary gas tube. Preferably, a voltage source is arranged to effect a potential difference between the electrospray nebuliser and the counter electrode. A controller may be arranged to control the voltage source to effect a DC potential difference, a potential difference of substantially fixed magnitude but alternating polarity, an alternating potential difference, or a combination of these.

In use, the nebulised sample is supplied from the electrospray nebuliser at an electrospray current, and the controller may in some embodiments be arranged to maintain the electrospray current at a substantially constant value.

Preferably, a first gas supply of a first gas of relatively high electron affinity, such as nitrogen, is arranged to be supplied at or around the electrospray nebuliser and a second gas supply of a second gas of relatively low electron affinity, such as argon, is arranged to be supplied to the nebulised sample upstream of the sample excitation region.

Preferably, a scavenging gas supply of an electron-scavenging gas, such as one or more of sulphur hexafluoride, oxygen and benzene, is arranged to be supplied to the sample introduction stage.

To help reduce or prevent surface charging effects, a nebulised sample discharging means, for neutralising the nebulised sample downstream of the electrospray nebuliser may be provided.

Preferably, the sample excitation stage comprises a plasma generator arranged to generate a plasma at the sample excitation region. This may be an ICP—preferably a(n industry) standard ICP—a MIP, or a glow discharge plasma generator. Alternatively, the sample excitation stage may comprise a flame excitation source for optical spectrometric analysis of the sample, such as for AAS or AES.

For some embodiments using chromatography or electrophoresis, the apparatus may further comprise a chromatographic or electrophoretic device arranged to supply the sample to the electrospray nebuliser.

According to a second aspect of the invention, there is provided a method of exciting a sample for spectrometric analysis, comprising generating a nebulised sample from an electrospray nebuliser; and receiving and exciting the nebulised sample at a sample excitation region operated in an atmospheric pressure environment.

According to a further aspect of the invention, there is provided the use of an electrospray nebuliser in combination with an ionisation or excitation source operated in an atmospheric pressure environment.

BRIEF DESCRIPTION OF THE DRAWINGS

The invention may be put into practice in a number of ways and some embodiments will now be described, by way of non-limiting example, with reference to the following figures, in which:

FIG. 1 shows schematically a sectional view of a conventional ICP source;

FIG. 2 shows schematically a sectional view of an embodiment with direct electrospray injection into a plasma;

FIG. 3 shows schematically a sectional view of an embodiment with electrospray injection into a spray chamber;

FIG. 4 shows schematically a sectional view of an embodiment with electrospray injection into an auxiliary gas tube;

FIG. 5 shows schematically a sectional view of an embodiment with electrospray injection into an auxiliary gas tube having a grid helper electrode; and FIG. 6 shows schematically a sectional view of an embodiment employing a glow discharge plasma.

DESCRIPTION OF PREFERRED EMBODIMENTS

Although the invention finds application more widely, the use of electrospray nebulisation with plasma ionisation in an atmospheric pressure environment, especially ICP, will now be discussed. Generally, an analyte solution is fed through a nebuliser capillary, or needle, having an outlet end. At least some of the solution discharged from the outlet end is fed to a plasma source. A potential difference is applied between the needle, its outlet end or the analyte solution itself and an effective electrode, which could be a tube, a grid or the plasma itself to promote the formation of smaller droplets. The pressure of the plasma source is similar to the pressure in the region just outside the needle outlet end; namely, there is less than a ten-fold pressure differential therebetween. For example, the electrospray nebuliser may operate at around 1 atm, while the plasma source operates at around 0.5 atm. Essentially, the plasma source operates in an atmospheric pressure environment.

FIG. 2 shows an arrangement in which an electrospray-nebulised sample is injected directly into a plasma. An electrospray needle 30 is held within an insulating injector 32 and is positioned a desired distance from a plasma region 34. A flow of a plasma gas 36, typically argon, surrounds the needle 30 concentrically, as a sheath gas, to keep the nebulised sample 38 in the hot, central part of the plasma region. A voltage differential is generated between the needle 30 and the plasma region 34 and this is typically of the order of +0.5 kV to +10 kV. For example, in many ICP-MS sources, the plasma is held substantially at ground potential, using source configurations known in the art. In this case, only a potential is applied to the needle 30 to enable electrospraying of small droplets directly into the plasma. This arrangement will work best if the desolvation capabilities of the plasma (through its heat and the gas flow through it) are sufficient to cope with the liquid sample load.

The potential difference to be applied depends on the flow rate of the sample in the electrospray nebuliser. Generally, the flow rate can be in the range from nanolitres per minute (nanospray), requiring only a few hundred volts of potential for a spray with small droplets of uniform size and a low variation of droplet size and composition over time, to several millilitres per minute, typically requiring a potential difference of several kilovolts for a typical spray distance of the order of lcm. That is, the required electric field is in the region up to 10 kV/cm.

By providing a strong electric field, an excess of charge is created at the end of the electrospray needle 30 containing the sample. The positive potential causes charge separation in the sample solution: anions travel towards the needle wall, while cations travel towards the meniscus of the droplet formed at the tip of the needle, forming a cone (the "Taylor cone"). When the electrostatic repulsion of the cations in the cone overcomes the surface tension of the solution, charged droplets are released from the tip. The positively charged droplets generally follow the electric field lines at the atmospheric pressure towards the counter electrode (in FIG. 2, the plasma itself), but can be affected by space charge and gas flow.

The Taylor cone effectively provides a reduced needle bore diameter, as the droplets are not formed immediately from the bore, but from the tip of the cone. This results in the generation of smaller sample droplets, which accordingly present a lower plasma load on the plasma generator, allowing for more stable operation.

Depending on operational requirements, a number of features may be varied to provide alternative configurations. For example, for high sample flow rates, a high-power atmospheric plasma, especially an ICP is preferred. This is because it is able to offer the most stable performance, even when the liquid flow or its ion content changes. Given the large region of the plasma at high temperature, the risk of the plasma being extinguished by, for example, the temporary admission of matter with greater heat capacity is reduced.

Conversely, for lower flow rates and variability of the analyte solution, the energy requirements for the plasma—that is, its power, density and size—are reduced. Accordingly, down to the limit of clogging the needle or the limit given by the desired dynamic range, a lower sample flow rate allows for a reduction in the size, power and pressure of the plasma. This, in turn, allows for a reduction in pressure for the overall electrospray and plasma region: the pressure could be $10^4$ Pa, $10^3$ Pa, down to several Pascals, or even lower, depending on the flow rate. A lower pressure or a smaller plasma size also affords a reduction in the flow rate of plasma gas (usually argon; occasionally helium) required to maintain a clean plasma and in the level of cooling required to prevent damage to components by the heat of the plasma.

The reduced-pressure alternative follows automatically when the sample liquid flow rate is reduced, as a result of improved nebulisation by electrospraying the sample from the needle. To avoid large pressure differentials between the sample introduction stage and the sample ionisation/excitation stage, the following features may be implemented in the plasma region. One clear feature is to seal the plasma region against the surrounding atmosphere. A vacuum pump may also pump through the opening of a sampler cone and/or a vacuum pump may (directly) pump the plasma region. The flow rates of the plasma and cooling gases may be reduced and also the liquid flow rate may be reduced. The lower the liquid flow rate, the less heat is required to convert the liquid to atomic ions. This, in turn, allows the plasma to operate with a reduced size and reduced power. Once the size and power of the plasma source are reduced, it is possible to reduce the plasma gas flow and the operating pressure. Reducing the pressure of the plasma region may also make extraction of the sample ions easier.

In some embodiments, it is not desirable for the plasma itself to form the counter electrode for the electrospray. In such a case, an additional electrode, for example a heat-resistant metal grid can be used. The grid could be made from tungsten, rhenium or rhodium, among others. With this arrangement, the spray characteristics can be made independent of the plasma conditions.

A further embodiment provides an arrangement in which a fluid splitter is disposed close to the electrospray needle tip. The sample liquid may thereby split between the plasma source and either a waste outlet or a recirculation device (so as not to use up too much sample). The purpose of this arrangement is to improve the liquid supply speed at low flow rates.

Figure 2:
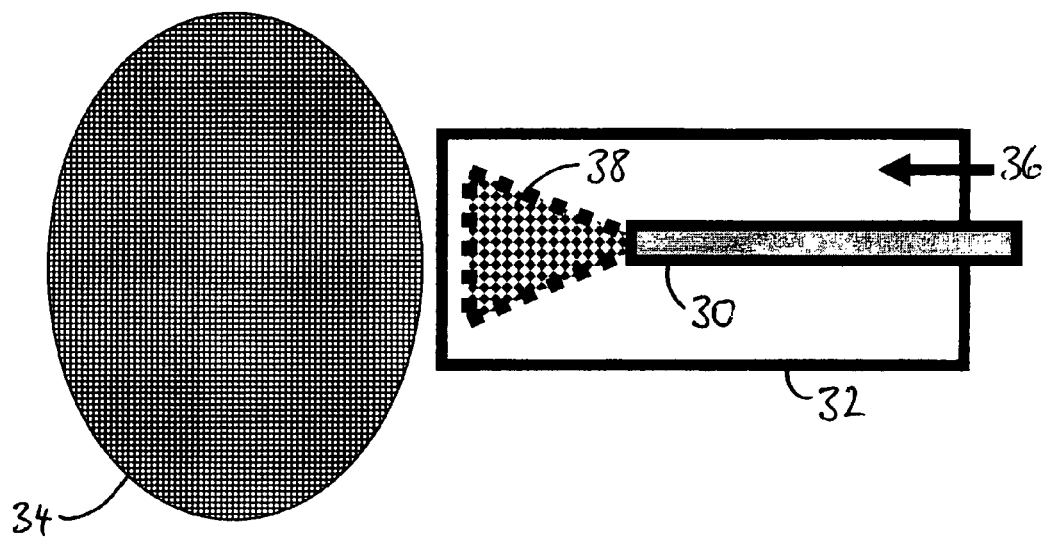
Figure 3:
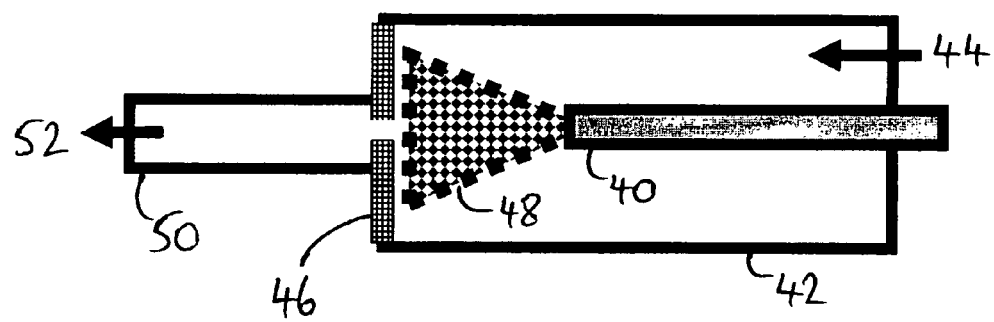

Starting from the direct injection shown in FIG. 2, the electrospray nebulisation can be provided anywhere upstream of the plasma. FIG. 3 shows an embodiment which is generally similar to the arrangement of FIG. 1, but with the conventional nebuliser 12 replaced by an electrically assisted nebuliser needle 40. The needle is located in an spray chamber 42, though which an argon sheath gas 44 is also arranged to flow. A counter electrode 46 draws the charged sample droplets 48 into an injector 50, which discharges them into a plasma region 52, for ionisation.

Generally, electro sprayed droplets are smaller and the droplet size variation has a lower standard deviation than droplets from conventional nebulisers. This is particularly advantageous when the spray is not otherwise sufficiently stable. The naturally improved droplet size and distribution reduce the need for additional separation of the droplets, as is known from the art; for example, in cooled cyclonic spray chambers where only small droplets are transmitted and bigger droplets are forced to cold walls from where they are drained. Of course, cyclonic spray chambers can still be used to further improve the droplet size distribution.

In the embodiment of FIG. 3, a standard ICP ionisation source, arranged for operation in an atmospheric pressure environment, has been modified with a new nebuliser arrangement: an electrically energised nebuliser needle 40 for generating charged droplets and a counter electrode 46 for extracting the charged droplets into the injector 50 for supply to the plasma region 52.

The use of electrospray nebulisation in itself is already known. In particular, the technique is used in the mass spectrometric analysis of large, organic (molecular) samples, in electrospray ionisation mass spectrometry (ESI-MS). Here, charged droplets are released from the Taylor cone, at the end of the electrospray needle, into an electrospray chamber. The eventual molecular ions are formed by desolvation of the positively charged droplets in the electrospray chamber, to remove the solvent from the droplets so that they increasingly shrink in size. When the charged droplets are sufficiently small, charge repulsion becomes important and Coulombic fission takes place, breaking the droplets up and reducing their size still further. These processes continue until molecular ions are left.

In addition to the requirement for a spray chamber in ESI-MS, a clean desolvation gas stream through the spray chamber is also required, as is a desolvation capillary or flow tube, which is usually heated, for transferring molecular ions to the downstream mass spectrometer. The two hardware elements—the spray chamber and especially the heated capillary—are costly and the desolvation gas stream contributes to an elevated cost per analysis.

One ESI-MS arrangement, disclosed in U.S. Pat. No. 7,005,635, has the above components, but the desolvation capillary has been modified with a reduced pressure region relative to the sample introduction chamber. A relatively small, low-power microwave-induced plasma (MIP) source is added to the arrangement, at the reduced pressure region, as a post-processing stage after the electrospray ionisation of the sample. The "significant pressure differential" between the sample introduction chamber and the plasma region is essential for allowing this MIP source to be added to the ESI-MS. It is also stated that current ICP sources cannot be integrated in an ESI-MS to provide the above post-processing. In any case, since (electrospray) ionisation takes place before the MIP source, the above approach requires a desolvation spray chamber with a desolvation gas flow, the heated capillary known from ESI—but in a modified form for the reduced pressure region—and the plasma support gas. It is thus relatively costly.

In significant contrast, the present invention provides sample ionisation or other sample excitation at an ionisation/excitation stage downstream of the sample introduction stage comprising the electrospray needle, with the ionisation/excitation stage operating in an atmospheric pressure environment (e.g., at or near atmospheric pressure). Electrospray ionisation is not the starting point for the invention, nor its objective, so the considerations for normal ESI do not need to be taken into account. This includes, in particular, the use of a desolvation capillary, which is not required: in an ICP source especially, the ability to decompose molecules completely to elemental form means that small clusters in droplets with solvent will be easily evaporated and atomised.

As previously discussed, unstable sample nebulisation directly affects the measurement accuracy and in serious cases leads to destabilisation of the plasma itself. With the use of an electrically energised nebuliser needle arrangement, the reduction in droplet size and droplet size variation can be sufficient to gain ICP sensitivity and stability better than with standard nebulisers. Thus the overall detection limit of the instrument can be improved, or the measurement time reduced.

Figure 4:
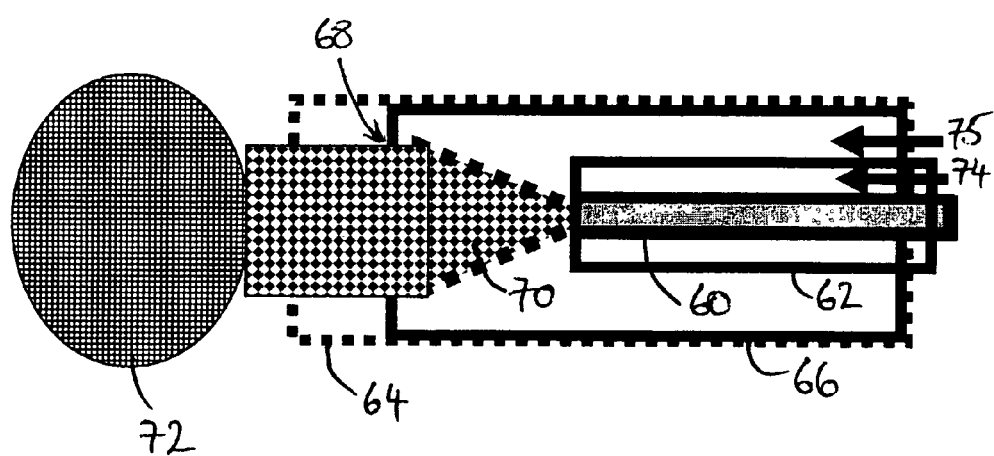

FIG. 4 shows an arrangement intermediate between the arrangement of FIG. 3, with injection into the spray chamber, and the arrangement of FIG. 2, with direct injection into the plasma region. In the arrangement of FIG. 4, the electrically nebulised sample is injected into an auxiliary gas tube, which is used as the counter electrode for the electrospray. The electrospray needle 60 is housed in an injector 62, which itself is housed in the auxiliary gas tube 64. Since the auxiliary gas tube 64 serves as the counter electrode, an insulator 66 is disposed within the tube and surrounding the electrospray needle 60. The insulator has a downstream opening 68, to allow the nebulised sample 70 to pass to the plasma region 72. In this way, the electrospray needle 60 is shielded from the electric field from the auxiliary gas tube 64 apart from at the insulator opening 68, which thereby acts to extract the charged droplets to the plasma. The auxiliary gas tube is made of a conductive metal, preferably platinum. Other metals alternatively be used, or a metal-coated or otherwise conductive auxiliary gas tube may be employed. Its potential is maintained at between −0.5 kV to −10 kV with respect to the electrospray needle 60, depending on the sample flow rate. Argon plasma carrier gas 74,75 serves to direct the sample into the centre of the plasma.

Figure 5:
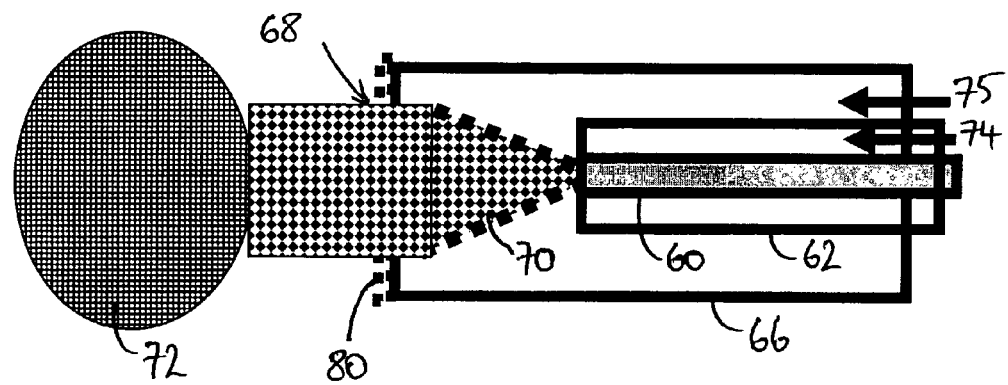

FIG. 5 shows a similar, but alternative arrangement, in which the counter electrode alternatively (although, in another embodiment, it may additionally) comprises a grid helper electrode 80, disposed at the outlet end of the auxiliary gas tube 64. The helper electrode could be a metal plate or a shielding electrode, such as a tungsten or tantalum grid.

The above configurations save on complex spray chambers, possibly also injectors, and there is no need for heated desolvation capillaries, since the plasma and high-temperature region around it provide sufficient heat for desolvation to occur anyway.

The above embodiments have the electrospray needle and the plasma/carrier gas flows parallel (generally concentric). However, it is desirable in some embodiments to configure the electrospray needle and the gas flow direction to the plasma region at certain angles with respect to each other; for example, 20°, 45°, 66° or 90°. This can be especially beneficial if it is desired to discard that part of the nebulised sample comprising the largest droplets, or if it is desired to select from the nebulised sample distribution preformed molecular ions.

It will be understood that, depending on the application and flow rate, different spray distances (from the nebuliser needle to the plasma region, for example) may be advantageous. For lower flow rates, the distances should generally be relatively small, starting from direct injection into the plasma and up to and beyond 1 cm distance; whereas, for higher flow rates, the distances should generally be longer.

The gas used in ICP sources is typically argon and it is convenient to use argon for injection and to assist in the nebulisation of the sample. The carrier gas can be directed in parallel flow with the injector, as a sheath gas. Alternatively, the carrier gas may be in counterflow and possibly pre-heated if it is desirable to provide additional desolvation. Reducing the sample droplet size in this region enables the size and power of the plasma source to be reduced. Alternatively still, the carrier gas may be directed at an arbitrary angle; for example, at an angle relative to both the electrospray needle and the injector. This can help to remove undesired portions of the sample spray, based on the charge and droplet size.

It will be appreciated that a balance may be found between the operating costs associated with external desolvation—additional heat sources and desolvating gas streams—and the operating costs associated with enabling the plasma to cope with a high sample load, including increasing the power consumption of the plasma source and increasing the amount of plasma gas used. This balance will vary depending on the particular application at hand.

As to the electrical energising of the nebuliser needle, depending on the flow rate of the sample, the spray voltage may range from around 500V to around 10 kV (e.g. 500V, 1 kV, 2 kV, 3 kV, 5 kV, and 10 kV). The voltage applied may be positive or negative. Appropriate selection of the polarity can promote the detection of specific components in a sample. The potential applied may be a fixed DC value, a value of substantially fixed magnitude but alternating polarity, a time-varying DC value, an AC voltage, or a combination of the above. More detail on this is provided below.

The electrical energising of the nebuliser needle and/or its co-operating counter electrode may be provided by a voltage source arranged to effect a potential difference therebetween. The voltage source may be provided by a signal generator (possibly connected with a signal amplifier) in combination with a high-voltage output transformer. The signal generator may be selected depending on the type of waveform, if any, desired. For example, a function generator (for producing simple repetitive waveforms, such as sine wave, sawtooth, step (pulse), square, and triangular waveforms) or an arbitrary waveform generator (for producing arbitrary, user-defined waveforms) may be used. A controller can be arranged to control the voltage source, to effect the desired DC or varying potential difference and/or to make real-time adjustments to the voltage source, in order, for example, to maintain the electrospray current of the nebulised sample at a substantially constant value.

One problem which has been recognised by the inventors when incorporating an electrospray nebuliser in an ICP source arrangement is pronounced arcing. This is caused by the fact that the plasma gas—usually argon—is selected precisely for the property of good plasma formation; that is, neutral argon has a low electron affinity, so is readily ionised. In contrast, conventional techniques using electrospray nebulisation typically take place in an air or nitrogen environment. Nitrogen has a relatively high electron capture cross section resulting in a significantly higher position on the Paschen curve (the plot of breakdown voltage in a particular gas against the pressure of that gas) relative to argon. Accordingly, the arcing problem does not significantly affect electrospray ionisation arrangements.

Given the widespread use of ICP sources, especially in mass spectrometry, many ICP operating parameters are subject to protocols and standardisation. It is accordingly highly desirable to implement the electrospray nebuliser sample introduction stage with a standard ICP sample excitation stage, rather than trying to introduce the industry to a new ICP operating regime. As such, the use of argon as the plasma gas should preferably be left unchanged.

According to the Paschen curve, arcing, through electrical breakdown of argon gas, becomes more likely when the pressure×length comes close to the minimum of the Paschen curve. It is accordingly undesirable to operate the system at a reduced pressure and operation in an atmospheric pressure environment is preferred. If desired, higher operating pressures could be used, to move to a still more favourable position on the Paschen curve (the alternative being use of extremely low voltages).

Another way of addressing the arcing, and consequential glow discharge, problem is by adjusting the inner and outer diameters of the electrospray nebulisation needle. Increasing the diameters reduces the sharpness of the needle tip, thereby reducing the occurrence of electrical breakdown in the vicinity of the tip. For example, an electrospray nebuliser needle, at 34 gauge (outer diameter: 0.18 mm; inner diameter: 0.1 mm), may be replaced by a needle at 32 gauge (outer diameter: 0.23 mm; inner diameter: 0.15 mm). With such a change, it may be desirable to supply the sample in a more diluted form, in order to keep the rate of supply of the analyte molecules/atoms the same at the increased liquid flow rate resulting from the change in diameter. It may also be desirable to reduce the surface tension of the liquid sample, by mixing it with tensid (e.g., Triton X-100).

An alternative approach is to use nitrogen as the carrier gas at the electrospray nebulisation stage and to introduce the argon subsequently; for example, in an auxiliary gas tube, upstream of the plasma source.

A further alternative way of addressing the above problem is to mix in with the argon carrier gas an electron scavenger, to reduce the conductive pathways for the arc/discharge. Suitable electron scavengers are sulphur hexafluoride ($SF_6$), benzene, oxygen, and benzene plus oxygen. Preferably, the electron scavenger employed will be readily decomposed in the downstream plasma.

As mentioned above, the voltage applied to the electrospray nebulisation needle may be alternated. This can help to avoid clogging of the needle and charge bias in the sample analysis. The frequency of alternation of the voltage could range from a few Hz to several kHz. Lower frequency alternation will generally help to avoid the clogging of the needle by ion separation and higher frequencies of alternation are advantageous in reducing a possible bias towards preformed positive or negative ions within polar solutions. It is understood that the droplet formation process for alternating current electrospray nebulisation appears to be different from DC nebulisation and does not necessarily involve a well-formed Taylor cone.

The use of alternating spray voltages also has an impact on the above arcing problem. Use of an alternating voltage can lead to a higher electric breakdown voltage in argon. Also, the different nebulisation mechanism with AC nebulisation, compared with DC nebulisation, provides a lower spray onset voltage, which is dependent on the frequency of the AC voltage. That is, lower peak voltages may be employed, reducing the likelihood of the argon breakdown voltage being reached.

Not all of the charged droplets sprayed from the electrically energised nebuliser needle are transferred to the excitation region (plasma, flame or other device), but instead come into contact with apparatus components between the electrospray needle and the excitation region. This can cause surface charging on those apparatus components, which can interfere with the nebulisation and/or subsequent passage to the excitation region of the sample. In order to reduce or prevent this charge-up, the nebulised sample droplets can be discharged downstream of the nebuliser needle. This can be achieved with an appropriately configured discharge grid or discharge needle.

The flow rate and composition of the carrier gas depend on the selection of the plasma source. For ICP sources, the gas used is typically argon; for MIP sources, the gas used is either helium or hydrogen. An ignition helper gas, such as oxygen, may be added, if desired. Also, if a smaller ICP source is desired, a counterflow argon carrier gas may be provided.

The sample liquid flow rate may lie in the range 1, 3, 5, 100, 200, 500 μl/min. The direct plasma injection arrangement has the potential of reducing the sample flow rate to a few nanolitres per minute. To improve the nebulisation of the sample further, instead of a normal solvent like a 2% aqueous solution of $HNO_3$, a purpose-made ionic liquid, such as ethylammonium nitrate or 1-butyl-3-methylimidazolium salts, could be used.

The invention may be applied to analysers and plasmas of all types, as mentioned above. The most straightforward implementation is for ICP-MS and ICP-OES, since these already make use of nebuliser, spray chamber, injector and torch arrangements. As such, little structural modification is required to implement the electrically assisted nebulisation technique.

Although plasma ionisation sources have been principally discussed above, the invention may also be applied to atomic emission spectroscopy and atomic absorption spectroscopy. AES uses flame excitation, instead of a plasma, to decompose molecules and stimulate atomic emissions, using the heat of the flame. The analyte emissions are detected using an optical spectrometer. In AAS, a cooler flame is used, so that the sample is desolvated and atomised, but the atoms are not excited out of their ground states. Light at various wavelengths is shone into the analysis region, simultaneously or sequentially, and the amount of light absorbed at a particular wavelength determines the amount of a particular analyte in the sample. In both cases, the use of electrically assisted nebulisation of the sample facilitates the desolvation and atomisation of the sample before optical analysis takes place.

The invention may also be applied to other ionisation techniques; for example, FIG. 6 shows an arrangement in which the ionisation source is a glow discharge plasma. US-A1-2007/0040112 describes a known glow discharge source.

The plasma source comprises an annular anode 82, disposed on top of an annular cathode 84 and separated by insulators 86,87 and insulating Peltier (cooling) elements 88. Argon plasma gas is provided to a supply tube 90 and passes into a central, plasma region 92. An outlet tube 94 is in communication with the plasma region 92 for exhausting gas therefrom.

At the lower end of the plasma region 92, an electrospray nebulisation needle 96 is provided, for supplying a nebulised sample into the plasma region. The argon gas is converted to a glow discharge plasma in the plasma region 92 and this plasma causes atomisation and ionisation of the nebulised sample as it is injected into the plasma region from the nebuliser needle 96. The (positive) sample ions are subsequently ejected from the glow discharge plasma source, by the action of the anode 82, towards a downstream mass spectrometer or other spectrometric analyser.

If desired, the nebuliser needle 96 could directly form part of the cathode of the glow discharge arrangement, with the annular cathode 84. Alternatively, the nebuliser needle 96 could be the sole cathode of the arrangement. If it is not desired to make the nebuliser needle 96 part of the electrode arrangement for the glow discharge plasma source, the sprayed droplets could be fed into the needle 96 to be introduced into the glow discharge source as a gas flow. This arrangement would work for both a DC and an RF glow discharge.

Figure 6:
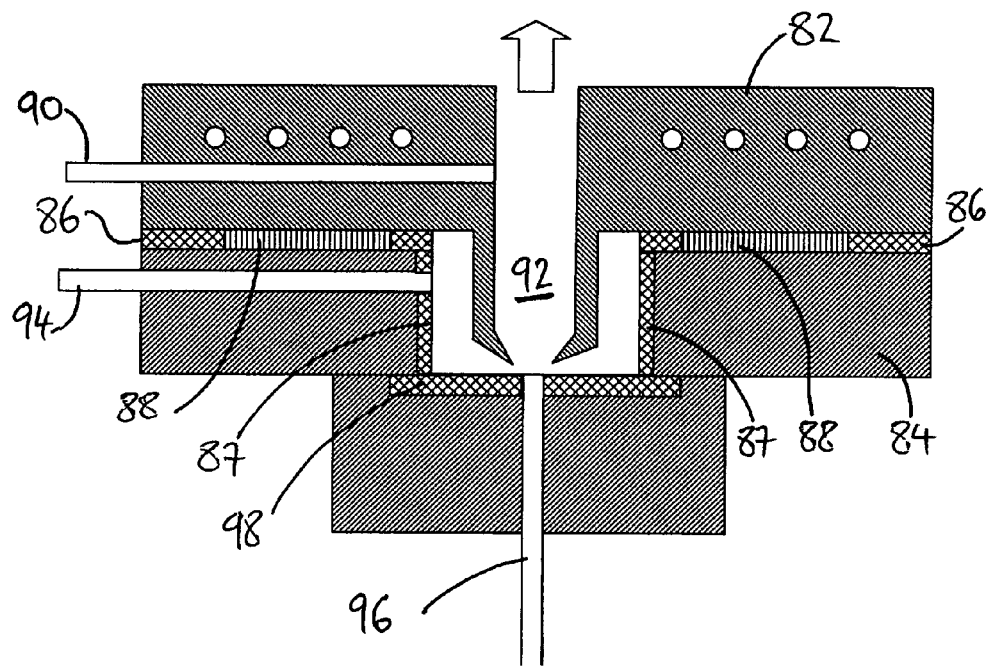

In some embodiments, it may be desirable to include a sacrificial electrode in the arrangement. Such an electrode, for example made from carbon, could be disposed around the outlet end of the nebuliser needle 96, as indicated in FIG. 6 under reference numeral 98.

Another glow discharge plasma source which may be used as a sample ionisation device in one embodiment of the invention is described in RU2211502.

In the above embodiments, various sample analyses can be performed. These include the analysis of trace metals, isotope ratios, toxic elements and traces; and analyses in the environmental (e.g., water, soil), semiconductor, biomedical (e.g., blood-plasma, urine), petrochemical, food, nuclear (e.g., isotopes), and geochemical fields. The electrospray nebuliser may also be coupled to upstream chromatographic devices, for use in liquid chromatography, HPLC and UHPLC ((ultra) high-performance liquid chromatography), ion exchange chromatography and electrophoresis. The separated analyte(s) can then be fed to the electrospray nebuliser, for subsequent analysis.

Embodiments of the invention provide the possibility of reducing the total cost of ownership of, for example, an ICP-MS, by reducing the amount of argon used and by reducing the plasma size, thereby decreasing the power requirement of the plasma source. Generally, embodiments of the invention provide a simplified and less expensive sample introduction assembly. By providing improved nebulisation of a sample, it is possible to improve the stability of the plasma and thereby to improve measurement sensitivity. Since the nebulised droplet size is reduced, the total volume of sample used per analysis may be reduced. Since it is not necessary to provide a special nebuliser tip to the needle—a straight tube ending for the nebuliser needle being acceptable—a lower minimum flow rate (to prevent clogging of the needle) can be achieved. This is especially so in combination with variation of the voltage applied to the nebuliser needle, to prevent electrochemical clogging.

The invention claimed is:

1. An inductively coupled plasma sample ionisation apparatus for a spectrometric analyser, the apparatus comprising:
   a sample introduction stage comprising an electrospray nebuliser for generating a nebulised sample;
   a sample ionisation stage comprising an inductively coupled plasma generator arranged to operate in an atmospheric pressure environment and to generate an inductively coupled plasma at a sample ionisation region, the sample ionisation region being arranged to receive and ionise the nebulised sample for spectrometric analysis thereof;
   a voltage source arranged to effect a potential difference between the electrospray nebuliser and a counter electrode; and
   a controller arranged to control the voltage source to effect a DC potential difference, wherein, in use, the nebulised sample is supplied from the electrospray nebuliser at an electrospray current, and the controller is arranged to maintain the electrospray current at a substantially constant value.

2. The apparatus of claim 1, wherein the electrospray nebuliser is arranged to discharge the nebulised sample directly into the sample ionisation region.

3. The apparatus of claim 2, wherein the sample ionisation region is configured with a potential difference relative to the electrospray nebuliser, so as to serve as a counter electrode.

4. The apparatus of claim 1, wherein the sample introduction stage further comprises a spray chamber and the electrospray nebuliser is arranged to discharge the nebulised sample into the spray chamber.

5. The apparatus of claim 4, wherein the spray chamber comprises a counter electrode disposed downstream of the electrospray nebuliser.

6. The apparatus of claim 1, wherein the sample introduction stage further comprises an auxiliary gas tube and the electrospray nebuliser is arranged to discharge the nebulised sample into the auxiliary gas tube.

7. The apparatus of claim 6, wherein the auxiliary gas tube is configured as a counter electrode, or comprises a counter electrode disposed downstream of the electrospray nebuliser.

8. The apparatus of claim 1, further comprising:
   a voltage source arranged to effect a potential difference between the electrospray nebuliser and the counter electrode; and
   a controller arranged to control the voltage source to effect an alternating potential difference.

9. The apparatus of claim 1, further comprising a first gas supply of a first gas of relatively high electron affinity arranged to be supplied at or around the electrospray nebuliser and a second gas supply of a second gas of relatively low electron affinity arranged to be supplied to the nebulised sample upstream of the sample ionisation region.

10. The apparatus of claim 9, wherein the first gas is nitrogen and the second gas is argon.

11. The apparatus of claim 1, further comprising a scavenging gas supply of an electron-scavenging gas arranged to be supplied to the sample introduction stage.

12. The apparatus of claim 11, wherein the electron-scavenging gas comprises one or more of sulphur hexafluoride, oxygen and benzene.

13. The apparatus of claim 1, further comprising a nebulised sample discharging means, for neutralising the nebulised sample downstream of the electrospray nebuliser.

14. The apparatus of claim 1, wherein the plasma generator is a standard ICP generator.

15. The apparatus of claim 1, further comprising a chromatographic or electrophoretic device arranged to supply the sample to the electrospray nebuliser.

16. A method of ionising a sample for spectrometric analysis, comprising:
   generating a nebulised sample from an electrospray nebuliser;
   receiving and ionising the nebulised sample at an inductively coupled plasma sample ionisation region operated in an atmospheric pressure environment; and
   effecting a DC potential difference between the electrospray nebuliser and a counter electrode, wherein the nebulised sample is supplied from the electrospray nebuliser at a substantially constant electrospray current.

17. The method of claim 16, wherein the nebulised sample is discharged directly into the sample ionisation region.

18. The method of claim 16, wherein the nebulised sample is discharged into a spray chamber.

19. The method of claim 16, wherein the nebulised sample is discharged into an auxiliary gas tube.

20. The method of claim 16, comprising effecting an alternating potential difference between the electrospray nebuliser and a counter electrode.

21. The method of claim 16, further comprising supplying a first gas of relatively high electron affinity at or around the electrospray nebuliser and supplying a second gas of relatively low electron affinity to the nebulised sample upstream of the sample ionisation region.

22. The method of claim 21, wherein the first gas is nitrogen and the second gas is argon.

23. The method of claim 16, further comprising supplying an electron-scavenging gas during the generating step.

24. The method of claim 23, wherein the electron-scavenging gas comprises one or more of sulphur hexafluoride, oxygen and benzene.

25. The method of claim 16, further comprising discharging the nebulised sample downstream of the electrospray nebuliser.

* * * * *